(12) United States Patent
Lim et al.

(10) Patent No.: US 7,915,436 B2
(45) Date of Patent: Mar. 29, 2011

(54) PHOSPHORUS-CONTAINING SILSESQUIOXANE DERIVATIVES AS FLAME RETARDANTS

(75) Inventors: Lisa S. Lim, Austin, TX (US); Eumi Pyun, Austin, TX (US); Joseph D. Rule, Cottage Grove, MI (US)

(73) Assignee: 3M Innovative Properties Company, St. Paul, MN (US)

( * ) Notice: Subject to any disclaimer, the term of this patent is extended or adjusted under 35 U.S.C. 154(b) by 218 days.

(21) Appl. No.: 12/263,704

(22) Filed: Nov. 3, 2008

(65) Prior Publication Data

US 2010/0113659 A1 May 6, 2010

(51) Int. Cl.
*C07F 9/02* (2006.01)
*C08F 283/00* (2006.01)
*C08G 77/04* (2006.01)

(52) U.S. Cl. .......... 556/405; 525/474; 525/476; 528/30; 528/33

(58) Field of Classification Search .................... 524/80; 525/474, 476; 528/30, 33
See application file for complete search history.

(56) References Cited

U.S. PATENT DOCUMENTS

| | | | | | |
|---|---|---|---|---|---|
| 2,843,615 | A | * | 7/1958 | Linville ........................ | 556/405 |
| 3,816,550 | A | * | 6/1974 | Young et al. ................. | 568/898 |
| 3,901,833 | A | * | 8/1975 | Flynn .......................... | 528/406 |
| 4,617,344 | A | * | 10/1986 | Tanaka et al. ................ | 524/837 |
| 5,627,296 | A | * | 5/1997 | Dauth et al. ................. | 556/405 |
| 5,652,026 | A | | 7/1997 | Saka et al. | |
| 6,362,279 | B2 | | 3/2002 | Lichtenhan et al. | |
| 6,518,357 | B1 | | 2/2003 | Rajagopalan et al. | |
| 6,534,601 | B1 | | 3/2003 | Park et al. | |
| 2004/0068074 | A1 | | 4/2004 | Yoshida et al. | |
| 2004/0077889 | A1 | * | 4/2004 | Sullivan et al. ................. | 556/13 |
| 2005/0033077 | A1 | | 2/2005 | Yamahiro et al. | |
| 2006/0252890 | A1 | | 11/2006 | Romenesko et al. | |

FOREIGN PATENT DOCUMENTS

| | | |
|---|---|---|
| CN | 101007824 A | 8/2007 |
| WO | WO 2005/078012 A2 | 8/2005 |
| WO | WO 2007/093588 A1 | 8/2007 |

OTHER PUBLICATIONS

Eisenberg et al., "Cagelike Precursors of High-Molar-Mass Silsesquioxanes Formed by the Hydrolytic Condensation of Trialkoxysilanes" Macromolecules, 33, 2000, pp. 1940-1947.

Li et al., "Viscoelastic and Mechanical Properties of Epoxy/Multifunctional Polyhedral Oligomeric Silsesquioxane Nanocomposites and Epoxy/Ladderlike Polyphenylsilsesquioxane Blends" Macromolecules, 34, 2001, pp. 8686-8693.

"UL Standard for Safety for Test for Flammability of Plastic Materials for Parts in Devices and Appliances" Underwriters Laboratories Inc. (UL) 2001, pp. 1-2, tr3, 14-18 (section 8—Jun. 2000 revision).

ASTM E 1354 -08 "Standard Test Method for Heat and Visible Smoke Release Rates for Materials and Products Using an Oxygen Consumption Calorimeter" 2008, pp. 1-19.

Pyun et al., "Composition, Method Of Making The Same, And Use Therefor", U.S. Appl. No. 61/103,288, filed Oct. 7, 2008.

PCT International Search Report, PCT/US2009/062912, mailing date Jan. 13, 2010.

Pyun et al., "Composition, Method Of Making The Same, And Use Therefor", U.S. Appl. No. 12/573,197, filed Oct. 5, 2009.

* cited by examiner

*Primary Examiner* — Randy Gulakowski
*Assistant Examiner* — Robert Loewe
(74) *Attorney, Agent, or Firm* — Bradford B. Wright

(57) ABSTRACT

A phosphorus-containing silsesquioxane is represented by the formula

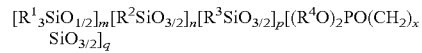

wherein each of $R^1$, $R^2$, $R^3$, and $R^4$ independently represents a hydrocarbyl group; x represents an integer of from 1 to 8; m is a positive number less than 1.5; n and q are positive numbers greater than 0 and less than 1; and p is a number greater than or equal to 0 and less than 1. Further, $(n+p)/q$ is in a range of from 0.5 to 99, and $(n+p+q)=1$. Curable and cured compositions comprising the phosphorus-containing silsesquioxane are disclosed.

9 Claims, No Drawings

PHOSPHORUS-CONTAINING SILSESQUIOXANE DERIVATIVES AS FLAME RETARDANTS

TECHNICAL FIELD

The present disclosure broadly relates to flame retardants and their use in epoxy resins.

BACKGROUND

Current flame retardants used in epoxy resins have a number of problems. For example, brominated and other halogen-containing flame retardants typically produce toxic and corrosive combustion products. Inorganic hydrates, which typically decompose to produce water, must typically be used in such high amounts that they compromise the physical properties of the epoxy resin. Moreover, halogen-based fire retardants have been the subject of various environmental regulatory concerns.

SUMMARY

The present disclosure provides a phosphorus-containing silsesquioxane represented by the formula

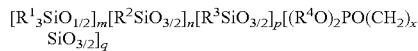

wherein
  each of $R^1$, $R^2$, $R^3$, and $R^4$ independently represents a hydrocarbyl group;
  x represents an integer of from 1 to 8;
  m is a positive number less than 1.5;
  n and q are positive numbers greater than 0 and less than 1; and
  p is a number greater than or equal to 0 and less than 1, wherein (n+p)/q is in a range of from 0.5 to 99, and further wherein (n+p+q)=1.

In some embodiments, each of $R^1$, $R^2$, $R^3$, and $R^4$ independently represents an alkyl group having from 1 to 8 carbon atoms. In some embodiments, each $R^1$ represents a methyl group, and each $R^2$ and $R^3$ is independently selected from the group consisting of a methyl group, a cyclohexyl group, a cyclopentyl group, and an isopropyl group. In some embodiments, x is 2. In some embodiments, the phosphorus-containing silsesquioxane has a number average molecular weight in a range of from 500 to 10000 grams per mole. In some embodiments, the phosphorus-containing silsesquioxane has a number average molecular weight in a range of from 1000 to 4000 grams per mole.

Silsesquioxanes according to the present disclosure are useful; for example, as flame retardants, and are especially useful in combination with non-halogen flame retardants.

Accordingly, in another aspect, the present disclosure provides a curable composition comprising an epoxy resin, an effective amount of curative for the polyepoxide, and a phosphorus-containing silsesquioxane according to the present disclosure.

In some embodiments, the curable composition further comprises an effective amount of curative for the thermosetting resin. In some embodiments, the thermosetting resin comprises a curable epoxy resin.

And in yet another aspect, the present disclosure provides a cured composition comprising a thermoset resin and a phosphorus-containing silsesquioxane according to the present disclosure.

As used herein:
  "hydrocarbyl group" refers to a univalent group formed by removing a hydrogen atom from a hydrocarbon;
  "non-halogenated" means free of halogen atoms;
  "thermosetting" means capable of being chemically crosslinked; and
  "thermoset" means sufficiently chemically crosslinked that it will not exhibit melt flow.

DETAILED DESCRIPTION

Silsesquioxanes have frameworks formed of Si—O—Si linkages. They are commonly formed by condensation of one or more organosilanes (e.g., trialkoxysilane derivatives).

Silsesquioxanes according to the present disclosure are represented by the formula

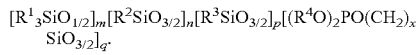

Each of $R^1$, $R^2$, $R^3$, and $R^4$ independently represents a hydrocarbyl group. Useful hydrocarbyl groups include aliphatic groups (e.g., linear, cyclic, and/or branched alkyl groups) and aromatic (e.g., aryl, aralkyl, or alkaryl groups) groups. Exemplary hydrocarbyl groups include: alkyl groups having from 1 to 8 carbon atoms such as, for example, methyl, ethyl, propyl, isopropyl, butyl, pentyl, hexyl, isooctyl, cyclohexyl, methylcyclohexyl, and cyclopentyl groups; aryl groups such as, for example, phenyl; aralkyl groups such as for example, methylphenyl and ethylphenyl groups; and aralkyl groups such as phenylethyl and phenylmethyl groups. Those embodiments in which $R^1$ is a methyl group are typically desirable. Similarly, those embodiments in which $R^2$ and $R^3$ independently represent methyl group(s), cyclohexyl group(s), cyclopentyl group(s), and isopropyl group(s) are typically desirable, especially in combination with $R^1$ being a methyl group.

The variable x represents an integer of from 1 to 8; for example, 1, 2, 3, 4, 5, 6, 7, or 8. Those embodiments in which x is 2 are typically desirable.

The variable m represents a positive number (i.e., any number greater than zero) less than 1.5; for example, 0.001, 0.01, 0.1, 0.3, 0.5, 0.75, 1, 1.25, or 1.49.

The variables n and q represent positive numbers that are greater than 0 and less than 1; for example, 0.01, 0.1, 0.3, or 0.5.

The variable p is a number greater than or equal to 0 and less than 1; for example 0, 0.01, 0.1, 0.3, 0.5, 0.75, or 0.99.

The variables x, m, n, p, and q, may be used in any combination subject to two constraints:
  (1) the quantity (n+p)/q is in a range of from 0.5 to 99; and
  (2) the quantity (n+p+q) equals 1.

The phosphorus-containing silsesquioxane may have any molecular weight meeting the abovementioned criteria. As is typical with silsesquioxanes, they may exist as a single compound or as mixture of silsesquioxanes having different molecular weights. In such cases, it is common practice in the art to refer to an average molecular weight (e.g., a number average molecular weight). Silsesquioxanes having a number average molecular weight in a range of from 500 to 10000 grams per mole (e.g., 1000 to 4000 grams per mole) are typically particularly suitable for use as flame retardants in thermosetting resins.

Silsesquioxanes according to the present disclosure may be made, for example, by condensation of corresponding trialkoxysilanes, which may be prepared according to known methods or purchased from commercial sources. In a representative synthesis, the trialkoxysilane derivatives are combined with formic acid and heated at elevated temperature (e.g., about 80° C.) sufficient to remove alcoholic byproducts generated by condensation of the trialkoxysilanes to form the corresponding silsesquioxane. Any residual silanol groups can be capped with $(CH_3)_3Si$— groups; for example, by addition of hexamethyldisilazane or hexamethyldisiloxane. Volatiles (including any unreacted starting materials) can be removed by heating under vacuum.

Respective amounts of n, p, and q can be controlled by controlling the amount of the corresponding trialkoxysilanes.

Silsesquioxanes according to the present disclosure are useful; for example, as flame retardants, and are especially useful in combination with non-halogenated flame retardants, wherein it may be possible to lower the overall amount by weight of the flame retardant that is necessary to pass industry standard tests for flame retardancy; for example, to obtain a UL94-V0 rating of a thermoset resin (according to test method UL 94 "Standard for Tests for Flammability of Plastic Materials for Parts in Devices and Appliances", Section 8, 20 mm Vertical Burning Test (updated through May 22, 2001) issued by Underwriters Laboratories of Northbrook, Ill.). Examples of non-halogenated flame retardants include: boehmite, organoborates, organophosphates, organophosphites, and organophosphinates (e.g., as EXOLIT OP1230 and EXOLIT OP930 available from Clariant Corp. of Charlotte, N.C.).

The present disclosure also provides a curable composition comprising a thermosetting resin, optionally an effective amount of curative for the thermosetting resin, and a phosphorus-containing silsesquioxane according to the present disclosure. Examples of thermosetting resins include epoxy resins (one-part and/or two-part), urethane resins (one-part and/or two-part), cyanate resins, phenolic resins, and acrylic resins. Desirably, for electronics applications the thermosetting resin is electronic grade.

Exemplary thermosetting resins include a two-part epoxy resin available as 3M SCOTCHCAST ELECTRICAL INSULATING RESIN 4 from 3M Company of Saint Paul, Minn. Examples of useful epoxy resins include 2,2-bis[4-(2,3-epoxypropoxy)-phenyl]propane (diglycidyl ether of bisphenol A) and materials available as EPON 828, EPON 1004, and EPON 1001F, commercially available from Shell Chemical Co., DER-331, DER-332 and DER-334, commercially available from Dow Chemical Co. Other suitable epoxy resins include glycidyl ethers of phenol formaldehyde novolac (e.g., DEN-43 and DEN-428, commercially available from Dow Chemical Co.).

Optionally, the thermosetting resin may contain one or more hardeners, initiators and/or catalysts (collectively referred to herein as "curative"), typically in an amount that is effective for chemically cross-linking the thermosetting resin (i.e., and effective amount of curative). The choice of curative and the amount to use typically will depend on the type of thermosetting resin selected, and will be well known to the skilled artisan. Exemplary curatives for epoxy resins include amines (including imidazoles), mercaptans, and Lewis acids.

The phosphorus-containing silsesquioxane may be in used in any amount in curable and/or cured compositions according to the present disclosure. For example, the phosphorus-containing silsesquioxane may be present in an amount in a range of from 1 to 20 percent by weight, typically 4 to 10 percent by weight, and more typically 4-8 percent by weight, based on the total weight of the curable and/or cured composition.

The curable compositions may be formed by simple mixing; however, it is generally desirable to use a technique capable of forming a uniform dispersion. In one technique, flame retardant and/or phosphorus-containing silsesquioxane are mixed into the thermosetting resin using a high shear mixer such as, for example, a high speed mixer available as SPEEDMIXER DAC 150FVZ from FlackTek, Inc. of Landrum, S.C.

The curable compositions may be cured, for example by conventional methods well known in the art, including by mixing (in the case of two-part thermosetting resins), heating, exposure to actinic or thermal radiation, or any combination thereof resulting in a cured composition Objects and advantages of this disclosure are further illustrated by the following non-limiting examples, but the particular materials and amounts thereof recited in these examples, as well as other conditions and, details, should not be construed to unduly limit this disclosure.

EXAMPLES

Unless otherwise noted, all parts, percentages, ratios, etc. in the Examples and the rest of the specification are by weight.

Materials used in the example are listed in Table 1 (below).

TABLE 1

Hexyltrimethoxysilane was obtained from TCI America of Portland, Oregon.
Methyltrimethoxysilane was obtained from Aldrich Chemical Co. of Milwaukee, Wisconsin.
Hexamethyldisiloxane, hexamethyldisilazane, and formic acid were obtained from Alfa-Aesar Co. of Ward Hill, Massachusetts.
Diethylphosphatoethyltriethoxysilane was obtained from Gelest Inc., of Morrisville, Pennsylvania.
SC4 refers to 3M SCOTCHCAST ELECTRICAL INSULATING RESIN 4, which is a two-part epoxy resin obtained from 3M Company of St. Paul, Minnesota.
OP1230 refers to EXOLIT OP1230 a flame retardant based on a metal organophosphinate salt obtained from Clariant Corp. of Charlotte, North Carolina.

UL94 20 mm Vertical Burn Test

The UL 94 "Standard for Tests for Flammability of Plastic Materials for Parts in Devices and Appliances", Section 8, 20 mm Vertical Burning Test (updated Jun. 8, 2000) issued by Underwriters Laboratories of Northbrook, Ill. was used, except that only the indicated number of replicates were tested. Summary criteria for the test are given in Table 2 (below):

TABLE 2

| CRITERIA CONDITIONS | 94 V-0 | 94 V-1 | 94 V-2 |
|---|---|---|---|
| Flame Time, T1 or T2 | ≦10 seconds | ≦30 seconds | ≦30 seconds |
| Flame Time, T1 + T2 | ≦50 seconds | ≦250 seconds | ≦250 seconds |
| Glow Time, T3 | ≦30 seconds | ≦60 seconds | ≦60 seconds |
| Did the specimen burn up to holding clamp? Yes/No | No | No | No |
| Did the specimen drip flaming particles that ignited the cotton indicator? Yes/No | No | No | Yes |

In Table 2 (above) $T_1$ refers to the afterflame time after first flame application. $T_2$ refers to the afterflame time after second flame application time. $T_3$ refers to the afterglow time after second flame application.

Cone Calorimeter Burn Test

Cone Calorimeter burn test were done in accordance to ASTM E1354-08, "Standard Test Method for Heat and Visible Smoke Release Rates for Materials and Products Using an Oxygen Consumption Calorimeter" (2008). Fire Growth Rate (FIGRA), which is not included in ASTM E1354-08 was calculated as the peak heat release rate divided by the time to peak heat release. Percent Reduction of FIGRA was determined using a control specimen tested on the same day as the test specimen.

Comparative Example A

Methyltrimethoxysilane (100 grams, 0.73 mole), hexyltrimethoxysilane (151.5 grams, 0.73 mole), and formic acid (202.7 grams, 4.40 moles) were placed in a 1-liter round bottom flask with magnetic stirring. The flask was heated in a 70° C. oil bath for 35 minutes with distillation to collect the volatile byproducts. Hexamethyldisiloxane (96 grams, 0.59 mole) was then added and the solution was heated in a 65° C. oil bath at reflux for 50 minutes. Volatile byproducts were then removed under vacuum. Hexane (200 mL) and hexamethyldisilazane (97 g, 0.60 mole) were added and the solution was suction filtered. The volatile components of the filtrate were removed under vacuum, first at room temperature and then with heating in a 90° C. oil bath. The resulting product, Comparative Silsesquioxane A, was a viscous, colorless liquid. $^1$H NMR analysis was consistent with the following formula:

$[(CH_3)_3SiO_{1/2}]_{0.4}[CH_3SiO_{3/2}]_{0.5}[C_6H_{13}SiO_{3/2}]_{0.5}$.

The number average molecular weight was measured by GPC relative to polystyrene standards as 680 grams/mole.

Example 1

Methyltrimethoxysilane (15 grams, 0.110 mole), hexyltrimethoxysilane (22.7 grams, 0.110 mole), diethylphosphatoethyltriethoxysilane (11.9 grams, 0.036 mole) and formic acid (35.4 grams, 0.770 mole) were combined in a 250-milliter round-bottomed flask, and magnetically stirred in an 80° C. oil bath with distillation of volatile byproducts over 25 minutes. Hexamethyldisiloxane (32 grams, 0.197 mole) was added and the mixture was stirred for an additional 65 minutes in the 80° C. oil bath. Volatile byproducts were removed under vacuum. Hexane (25 g) and hexamethyldisilazane (25 g, 0.155 mole) were then added and the solution was stirred for 35 minutes. The volatile products were removed under vacuum to give Silsesquioxane 1 as a viscous, colorless liquid. $^1$H NMR analysis was consistent with the formula:

$[(CH_3)_3SiO_{1/2}]_{0.38}[CH_3SiO_{3/2}]_{0.43}[C_6H_{13}SiO_{3/2}]_{0.43}$
$[(C_2H_5O)_2PO(CH_2)_2SiO_{3/2}]_{0.14}$

The number average molecular weight was measured by GPC relative to polystyrene standards as 1600 grams/mole.

Flame Retardancy Testing

Various thermosetting compositions were prepared and tested according to the UL94, 20 mm Vertical Burn Test by combining the indicated flame retardant(s) in SC4 epoxy resin in the amounts indicated in Tables 3 and 4 (below). All the compositions listed in Table 3 (below) had T3=0 seconds, did not burn to the holding clamp, and did not ignite cotton as in UL 94 above. All the parameters in Table 4 are as defined in ASTM E1354-08 except FIGRA (column 7 in Table 4). FIGRA=Fire growth rate and is calculated as the peak heat release rate (column 5 in Table 4) divided by the time to peak heat release rate (column 6 in Table 4). Reduction of FIGRA in Table 4 is the percentage difference in FIGRA for each row compared to the control 100 parts SC4 (row 1). In Table 4, MJ=megajoules; m$^2$=square meter; and kW=kilowatts. The cone calorimeter instrument measurements have a known error on the order of +/−10 percent.

TABLE 3

| EXAMPLE | THERMOSETTING COMPOSITION | REPLICATE | DRIP? | UL94 20 mm Vertical Burn Test PASS/FAIL V0-V2 |
|---|---|---|---|---|
| COMPARATIVE EXAMPLE B1 | 94 parts SC4, 6 parts OP1230 | 1 | No | Fail |
| | | 2 | No | Fail |
| | | 3 | No | Fail |
| | | 4 | No | Fail |
| COMPARATIVE EXAMPLE B2 | 93 parts SC4, 7 parts OP1230 | 1 | No | Fail |
| | | 2 | No | V1 |
| COMPARATIVE EXAMPLE B3 | 92 parts SC4, 8 parts OP1230 | 1 | No | V1 |
| | | 2 | No | V1 |
| COMPARATIVE EXAMPLE C | 93 parts SC4, 6 parts OP1230, 1 part Comparative Silsesquioxane A | 1 | No | V1 |
| | | 2 | No | V0 |
| EXAMPLE 2 | 93 parts SC4, 6 parts OP1230, 1 part Silsesquioxane 2 | 1 | No | V0 |
| | | 2 | No | V0 |
| EXAMPLE 3 | 99 parts SC4, 1 part Silsesquioxane 2 | 1 | No | Fail |
| | | 2 | No | Fail |
| EXAMPLE 4 | 93 parts SC4, 7 part Silsesquioxane 2 | 1 | No | Fail |
| | | 2 | No | V1 |

TABLE 4

| EXAMPLE | THERMOSETTING COMPOSITION | Total Heat Release, MJ/m$^2$ | Average. Heat Release Rate, kW/m$^2$ | Peak Heat Release Rate, kW/m$^2$ | Peak at time, seconds | FIGRA | Percent Reduction of FIGRA |
|---|---|---|---|---|---|---|---|
| COMPARATIVE EXAMPLE D | 100 parts SC4 | 175 | 920 | 2006 | 145 | 13.83 | 0.0 |
| COMPARATIVE EXAMPLE B1 | 94 parts SC4, 6 parts OP1230 | 150 | 484 | 707 | 205 | 3.45 | 75.6 |
| COMPARATIVE EXAMPLE B2 | 93 parts SC4, 7 parts OP1230 | 133 | 408 | 852 | 215 | 3.96 | 71.6 |
| COMPARATIVE EXAMPLE B3 | 92 parts SC4, 8 parts OP1230 | 129 | 389 | 710 | 230 | 3.09 | 77.8 |
| COMPARATIVE EXAMPLE C | 93 parts SC4, 6 parts OP1230, 1 part Comparative Silsesquioxane A | 150 | 698 | 1379 | 155 | 8.90 | 37.1 |

TABLE 4-continued

| EXAMPLE | THERMOSETTING COMPOSITION | Total Heat Release, MJ/m² | Average. Heat Release Rate, kW/m² | Peak Heat Release Rate, kW/m² | Peak at time, seconds | FIGRA | Percent Reduction of FIGRA |
|---|---|---|---|---|---|---|---|
| EXAMPLE 2 | 93 parts SC4, 6 parts OP1230, 1 part Silsesquioxane 2 1% S-2 | 145 | 425 | 639 | 210 | 3.04 | 78.0 |
| EXAMPLE 3 | 99 parts SC4, 1 part Silsesquioxane 2 | 162 | 662 | 1515 | 165 | 9.18 | 34.1 |
| EXAMPLE 4 | 93 parts SC4, 7 part Silsesquioxane 2 | 155 | 378 | 613 | 110 | 5.57 | 60.0 |

All patents and publications referred to herein are hereby incorporated by reference in their entirety. Various modifications and alterations of this disclosure may be made by those skilled in the art without departing from the scope and spirit of this disclosure, and it should be understood that this disclosure is not to be unduly limited to the illustrative embodiments set forth herein.

What is claimed is:

1. A curable composition comprising:
   a thermosetting resin;
   a non-halogenated flame retardant selected from the group consisting of organoborates, organophosphates, organophosphites, and organophosphinates; and
   a phosphorus-containing silsesquioxane represented by the formula $$[R^1{}_3SiO_{1/2}]_m[R^2SiO_{3/2}]_n[R^3SiO_{3/2}]_p[(R^4O)_2PO(CH_2)_xSiO_{3/2}]_q$$

wherein
      each of $R^1$, $R^2$, $R^3$, and $R^4$ independently represents a hydrocarbyl group;
      x represents an integer of from 1 to 8;
      m is a positive number less than 1.5;
      n and q are positive numbers greater than 0 and less than 1; and
      p is a number greater than or equal to 0 and less than 1, wherein (n+p)/q is in a range of from 0.5 to 99, and further wherein (n+p+q)=1.

2. The curable composition of claim 1, further comprising an effective amount of curative for the thermosetting resin.

3. The curable composition of claim 1, wherein the thermosetting resin comprises a curable epoxy resin.

4. The curable composition of claim 1, wherein each $R^1$ represents a methyl group; and each $R^2$ and $R^3$ is independently selected from the group consisting of a methyl group, a cyclohexyl group, a cyclopentyl group, and an isopropyl group, and x is 2.

5. The curable composition of claim 1, wherein the phosphorus-containing silsesquioxane has a number average molecular weight in a range of from 500 to 10000 grams per mole.

6. A cured composition comprising:
   a thermoset resin;
   a non-halogenated flame retardant selected from the group consisting of organoborates, organophosphates, organophosphites, and organophosphinates; and
   a phosphorus-containing silsesquioxane represented by the formula $$[R^1{}_3SiO_{1/2}]_m[R^2SiO_{3/2}]_n[R^3SiO_{3/2}]_p[(R^4O)_2PO(CH_2)_xSiO_{3/2}]_q$$

wherein
      each of $R^1$, $R^2$, $R^3$, and $R^4$ independently represents a hydrocarbyl group;
      x represents an integer of from 1 to 8;
      m is a positive number less than 1.5;
      n and q are positive numbers greater than 0 and less than 1; and
      p is a number greater than or equal to 0 and less than 1, wherein (n+p)/q is in a range of from 0.5 to 99, and further wherein (n+p+q)=1.

7. The curable composition of claim 6, wherein the thermosetting resin comprises a curable epoxy resin.

8. The cured composition of claim 6, wherein each $R^1$ represents a methyl group;
   and each $R^2$ and $R^3$ is independently selected from the group consisting of a methyl group, a cyclohexyl group, a cyclopentyl group, and an isopropyl group, and x is 2.

9. The cured composition of claim 6, wherein the phosphorus-containing silsesquioxane has a number average molecular weight in a range of from 500 to 10000 grams per mole.

* * * * *